(12) United States Patent
Hayashida et al.

(10) Patent No.: US 7,951,279 B2
(45) Date of Patent: May 31, 2011

(54) ELECTROPHORESIS APPARATUS AND DEVICE THEREFOR

(75) Inventors: Chie Hayashida, Taito-ku (JP); Koji Sakairi, Taito-ku (JP); Katsuyoshi Takahashi, Setagaya-ku (JP); Yuji Maruo, Nagareyama (JP); Michinobu Mieda, Shiki-gun (JP); Yutaka Unuma, Matsudo (JP)

(73) Assignees: Toppan Printing Co., Ltd., Tokyo (JP); Sharp Kabushiki Kaisha, Osaka-Shi, Osaka ( * ) Notice: Subject to any disclaimer, the term of this patent is extended or adjusted under 35 U.S.C. 154(b) by 864 days.

(21) Appl. No.: 11/663,646

(22) PCT Filed: Sep. 5, 2006

(86) PCT No.: PCT/JP2006/017491
§ 371 (c)(1),
(2), (4) Date: Mar. 23, 2007

(87) PCT Pub. No.: WO2007/029666
PCT Pub. Date: Mar. 15, 2007

(65) Prior Publication Data
US 2007/0278102 A1    Dec. 6, 2007

(30) Foreign Application Priority Data
Sep. 5, 2005  (JP) ................................. 2005-257125

(51) Int. Cl.
*G01N 27/453*    (2006.01)
(52) U.S. Cl. ........................................ 204/616; 204/606
(58) Field of Classification Search .................. 204/450, 204/456, 600, 606, 619, 620, 615, 616
See application file for complete search history.

(56) References Cited

U.S. PATENT DOCUMENTS

| | | | | | |
|---|---|---|---|---|---|
| 4,718,998 A | * | 1/1988 | Ogawa et al. | ................. | 204/606 |
| 4,748,050 A | * | 5/1988 | Takahashi et al. | ............ | 427/164 |
| 5,187,243 A | * | 2/1993 | Jordan et al. | ................. | 525/464 |
| 5,340,461 A | * | 8/1994 | Fukushige et al. | ............ | 204/607 |

(Continued)

FOREIGN PATENT DOCUMENTS

CA    2 433 103 A1    1/2004

(Continued)

OTHER PUBLICATIONS

International Search Report for PCT/JP2006/317491 mailed Dec. 5, 2006.

(Continued)

*Primary Examiner* — Kaj K Olsen
(74) *Attorney, Agent, or Firm* — Nixon & Vanderhye, PC (57) ABSTRACT

There is provided an electrophoresis device including an insulator that includes: a first-separating-medium storing section for storing therein a first separating medium; a first opening and a second opening that are in communication with the first-separating-medium storing section and for defining a direction of separation on the first separating medium; and a third opening that is covered with a penetrable insulating thin film, wherein the first separating medium storing section is in communication with outside via the first opening and the second opening. There is also provided an electrophoresis apparatus including the electrophoresis device. This realizes an electrophoresis apparatus, and a device therefor, that enables an operator to sample separated proteins without ever making contact with the electrophoresed gel, and that can easily be used with various types of analyses, thereby improving convenience of electrophoresis.

12 Claims, 6 Drawing Sheets

U.S. PATENT DOCUMENTS

| | | | |
|---|---|---|---|
| 5,399,255 A * | 3/1995 | Sarrine | 204/616 |
| 5,773,645 A * | 6/1998 | Hochstrasser | 204/456 |
| 6,013,165 A * | 1/2000 | Wiktorowicz et al. | 204/456 |
| 2002/0089625 A1 | 7/2002 | Grupp | |
| 2002/0179448 A1* | 12/2002 | Lauks | 204/600 |
| 2003/0180807 A1 | 9/2003 | Hess et al. | |
| 2004/0144647 A1 | 7/2004 | Dorner et al. | |
| 2004/0238364 A1* | 12/2004 | Salven et al. | 204/606 |
| 2005/0008541 A1 | 1/2005 | Hochstrasser et al. | |
| 2006/0210426 A1 | 9/2006 | Hagiwara | |
| 2007/0278102 A1 | 12/2007 | Hayashida et al. | |

FOREIGN PATENT DOCUMENTS

| | | |
|---|---|---|
| EP | 1 628 137 A1 | 2/2006 |
| JP | 5-215713 | 8/1993 |
| JP | 5-215713 A | 8/1993 |
| JP | 5-215714 A | 8/1993 |
| JP | 7-132079 A | 5/1995 |
| JP | 2004-053608 | 2/2004 |
| JP | 2004-53608 A | 2/2004 |
| JP | 2005/012916 A1 | 2/2005 |
| JP | 2005-030905 | 2/2005 |
| JP | 2005-30905 A | 2/2005 |
| JP | 2005-69905 A | 3/2005 |
| JP | 2005-77242 A | 3/2005 |
| JP | 2005-172621 A | 6/2005 |
| JP | 2005-215716 | 8/2005 |
| WO | 2005/012916 A1 | 2/2005 |

OTHER PUBLICATIONS

U.S. Appl. No. 11/663,670, filed Mar. 23, 2007, entitled Electrophoresis Apparatus and Device Therefore.

Machine translation of JP05-215713 A, 1993.

Machine translation of JP2005-030905A.

U.S. Office Action mailed Sep. 14, 2009 in co-pending U.S. Appl. No. 11/663,670.

U.S. Office Action mailed Dec. 2, 2010 in co-pending U.S. Appl. No. 11/663,670.

U.S. Office Action mailed Aug. 17, 2010 in co-pending U.S. Appl. No. 11/663,670.

U.S. Office Action mailed Mar. 4, 2010 in co-pending U.S. Appl. No. 11/663,670.

U.S. Office Communication (Advisory Action) mailed Mar. 23, 2011 in co-pending U.S. Appl. No. 11/663,670.

* cited by examiner

ELECTROPHORESIS APPARATUS AND DEVICE THEREFOR

This application is the US national phase of international application PCT/JP2006/317491 filed 5 Sep. 2006 which designated the U.S. and claims benefit of JP 2005-257125, dated 5 Sep. 2005, the entire content of which is hereby incorporated by reference.

TECHNICAL FIELD

The present invention relates to an electrophoresis apparatus and a device therefor. Specifically, the invention relates to an electrophoresis apparatus, and a device therefor, that can sensitively monitor a separating medium on site, and enables desired portions of the separating medium to be removed and conveniently used for further analysis.

BACKGROUND ART

In analyses using electrophoresis (for example, mass spectrometry), a cassette charged with an electrophoresis gel (separating medium) is placed in an electrophoresis chamber, and a sample that contains proteins (or DNA/RNA) is applied to the medium. After electrophoresis, the gel is removed from the cassette, and the stained gel is observed. A required portion of the gel is then cut out for analysis.

The electrophoresis gel used for the separation and development of the sample is thin and fragile. For the detection and/or quantification of the separated protein spots (bands) in the gel after the electrophoresis, it is required to (1) take out the cassette from the electrophoresis chamber, (2) disassembly the cassette and remove the gel, (3) transport the gel to a detection device (or place the gel on a flat immobilizing plate to transport it), and (4) dip the gel in a liquid (or immobilize on a support film) to prevent deformation. This is a complicated procedure, and it can be hazardous since the gel is toxic. Further, the procedure is time consuming because the gel is stained after the electrophoresis is finished. There have been proposed methods in which fluorescence-stained samples are used to omit the gel staining step and all other preceding steps (see Patent Publications 1 and 2, for example).

Patent Publication 1: Japanese Unexamined Patent Application Publication No. 215713/1993 (Tokukaihei 5-215713, published on Aug. 24, 1993).

Patent Publication 2: Japanese Unexamined Patent Application Publication No. 215714/1993 (Tokukaihei 5-215714, published on Aug. 24, 1993).

Patent Publication 3: Japanese Unexamined Patent Application Publication No. 132079/1995 (Tokukaihei 7-132079, published on May 23, 1995).

Patent Publication 4: Japanese Unexamined Patent Application Publication No. 69905/2005 (Tokukai 2005-69905, published on Mar. 17, 2005).

Patent Publication 5: Japanese Unexamined Patent Application Publication No. 77242/2005 (Tokukai 2005-77242, published on Mar. 24, 2005).

Patent Publication 6: Japanese Unexamined Patent Application Publication No. 172621/2005 (Tokukai 2005-172621, published on Jun. 30, 2005).

DISCLOSURE OF INVENTION

However, with the techniques described in Patent Publications 1 and 2, it is still required to cut a desired portion of the gel for analyses. Further, the techniques described in Patent Publications 3 through 6 require the complex procedures as mentioned in (1) to (4) above, and in some cases, staining the removed gel, or moving the gel from the detection device to a device used to cut the gel.

Since both of these two techniques require removing the gel from the cassette, an operator is in contact with the gel if the techniques were used together and performed continuously. That is, a person ordinary skill in the art cannot avoid contacting the gel. More specifically, there have been attempts to perform electrophoresis steps by machine or by automation. However, it has not been possible to perform detection without removing the gel from the cassette or cut a desired portion of the gel. Removing the gel diffuses the separated protein spots, or contaminates, dries, or deforms the gel. This has prevented a smooth transition from the electrophoresis to subsequent analysis steps.

The present invention was made in view of the foregoing problems, and an object of the invention is to realize an electrophoresis apparatus that enables an operator during or after the electrophoresis to easily observe separated proteins without ever making contact with the electrophoresed gel, and cut a desired portion of the gel at a desired timing for sampling.

Specifically, according to the present invention, there is provided an electrophoresis device including an insulator, wherein the insulator includes: a first-separating-medium storing section for storing therein a first separating medium; a first opening and a second opening that are in communication with the first-separating-medium storing section and for defining a direction of separation on the first separating medium; and a third opening that is covered with a penetrable insulating thin film.

The present invention relates to an electrophoresis device that retains a separating medium used for electrophoresis. With the foregoing structure, an electrophoresis device according to the present invention can store therein a first separating medium from which a sample can be collected as it is being separated. The sample can be collected at a desired timing while current is flown to separate the sample form the first opening toward the second opening.

In an electrophoresis device according to the present invention, it is preferable that the insulator include a first plate-insulator and the insulating thin film, and that the first-separating-medium storing section be a depression formed in the first plate-insulator, and the first separating medium be covered with the insulating thin film.

With the foregoing structure, an electrophoresis device according to the present invention is applicable to known slab gel electrophoresis apparatuses, and is able to store the first separating medium, with the opening of the depression shielded from outside by the insulating thin film.

An electrophoresis device according to the present invention includes an insulator, wherein the insulator includes: a first-separating-medium storing section storing therein a first separating medium; a first opening and a second opening that are in communication with the first-separating-medium storing section and for defining a direction of separation on the first separating medium; and a third opening that is covered with a penetrable insulating thin film.

With the foregoing structure, an electrophoresis device according to the present invention can store therein a first separating medium from which a sample can be collected as it is being separated. The sample can be collected at a desired timing while current is flown to separate the sample form the first opening toward the second opening in the first separating medium.

In an electrophoresis device according to the present invention, it is preferable that the insulator include a first plate-insulator and the insulating thin film, and that the first-separating-medium storing section be a depression formed in the first plate-insulator, and the first separating medium be covered with the insulating thin film.

With the foregoing structure, an electrophoresis device according to the present invention is applicable to known slab gel electrophoresis apparatuses, and is able to store the first separating medium, with the first separating medium shielded from outside by the insulating thin film.

In an electrophoresis device according to the present invention, it is preferable that the insulator further include a second plate-insulator, and that the first separating medium storing section be a depression formed in the first plate-insulator.

With the foregoing structure, an electrophoresis device according to the present invention can improve overall strength, and provide ease of handling that compares to the conventional slab gel.

In an electrophoresis device according to the present invention, it is preferable that the third opening be provided in the second plate-insulator.

In an electrophoresis device according to the present invention, the third opening may be formed in a substrate different from the one storing the first separating medium. This makes it easier to fabricate the first separating medium in the device, thereby sealing the first separating medium more easily.

In an electrophoresis device according to the present invention, it is preferable that the first plate-insulator or the insulating thin film be made of a light-transmissive material.

With the first plate-insulator or insulating thin film made of a light-transmissive material, an electrophoresis device according to the present invention is able to irradiate light or detect fluorescence through the first plate-insulator or the insulating thin film. This realizes a sampling procedure that enables the first separating medium to be detected in the first separating medium storing section and a desired part of the first separating medium to be cut out.

It is preferable that an electrophoresis device according to the present invention further include: a first buffer chamber for reserving a first buffer to be brought into contact with the first separating medium at the first opening; and a second buffer chamber for reserving a second buffer to be brought into contact with the first separating medium at the second opening.

Since an electrophoresis device according to the present invention is provided with the buffer chambers for reserving buffers necessary for the electrophoresis, there is no need to assemble the device with new buffer chambers.

In an electrophoresis device according to the present invention, it is preferable that the insulator, the first buffer chamber, and the second buffer chamber be formed in one piece.

Since an electrophoresis device according to the present invention is integrally provided with the buffer chambers for reserving buffers necessary for the electrophoresis, the device is easy to operate and/or carry around.

In an electrophoresis device according to the present invention, it is preferable that the first opening or the second opening be shaped to fit a second separating medium retaining a sample.

With the first opening or the second opening shaped to fit a second separating medium retaining a sample, an electrophoresis device according to the present invention ensures that the sample is moved to the first separating medium without fail, and thereby enables more reliable separation in the first separating medium.

With the foregoing structure, an electrophoresis device according to the present invention can supply the sample to the first separating medium after the sample has been separated on a different separating medium, thereby realizing the two-dimensional electrophoresis.

In an electrophoresis device according to the present invention, it is preferable that the first separating medium and the second separating medium have different separating parameters.

With the foregoing structure, an electrophoresis device according to the present invention has improved resolutions.

In an electrophoresis device according to the present invention, it is preferable that the insulating thin film have a thickness no greater than 1000 µm. Depending on the material of the film, the insulating thin film has a thickness of preferably no greater than 800 µm, more preferably no greater than 500 µm, and most preferably no greater than 125 µm.

In an electrophoresis device according to the present invention, it is preferable that the insulating thin film have a strike resistance of 1 mN to 50 mN.

In an electrophoresis device according to the present invention, it is preferable that the insulating thin film is any one of a polystyrene film, a polyethylene terephthalate film, a polyvinyl chloride film, a polyvinylidene chloride film, polyolefin resin film, and a polypropylene film.

An electrophoresis apparatus according to the present invention include the electrophoresis device, and cutting means for cutting a sample in the first separating medium.

With the foregoing structure, an electrophoresis apparatus according to the present invention is able to store the first separating medium, from which a sample can be collected at a desired timing as it is being separated.

It is preferable that an electrophoresis apparatus according to the present invention include: irradiating means for irradiating a sample in the first separating medium; and detecting means for detecting fluorescence from the sample.

With the foregoing structure, an electrophoresis apparatus according to the present invention allows the sample to be observed as it is being separated.

It is preferable that an electrophoresis apparatus according to the present invention further include first voltage applying means for applying voltage to the first separating medium.

In an electrophoresis apparatus according to the present invention, it is preferable that a first electrode and a second electrode to be respectively inserted in the first buffer chamber and the second buffer chamber be provided on first wiring means connected to the first voltage applying means.

With the electrodes independently provided from the buffer chambers, an electrophoresis apparatus according to the present invention can easily replace or wash the electrodes.

It is preferable that an electrophoresis apparatus according to the present invention further include moving means for moving the second separating medium, having a sample retained thereon, to the first opening or the second opening.

In order to prevent deformation or contamination of the gel, it is necessary that electrophoresis be performed without intervention of human hands. With the automated transport system realized by the moving means, an electrophoresis apparatus according to the present invention can realize automated two-dimensional electrophoresis.

In an electrophoresis apparatus according to the present invention, it is preferable that the first wiring means be moved by the moving means.

With the foregoing structure, an electrophoresis apparatus according to the present invention realizes automated two-dimensional electrophoresis by the automated transport system, without intervention of human hands.

It is preferable that an electrophoresis apparatus according to the present invention further include a separating device for separating a sample in the second separating medium, and that the moving means move from the separating device to the first opening or the second opening in the second separating medium.

With the foregoing structure, an electrophoresis apparatus according to the present invention realizes automated two-dimensional electrophoresis by the automated transport system, without intervention of human hands.

It is preferable that an electrophoresis apparatus according to the present invention further include second voltage applying means for applying voltage to the second separating medium.

With the foregoing structure, an electrophoresis apparatus according to the present, invention can realize automated two-dimensional electrophoresis.

In an electrophoresis apparatus according to the present invention, it is preferable that the third electrode to be inserted into the separating device be provided on second wiring means connected to the second voltage applying means.

With the foregoing structure, an electrophoresis apparatus according to the present invention realizes automated two-dimensional electrophoresis.

In an electrophoresis apparatus according to the present invention, it is preferable that the second wiring means be moved by the moving means.

With the foregoing structure, an electrophoresis apparatus according to the present invention can realize automated two-dimensional electrophoresis.

It is preferable that an electrophoresis apparatus according to the present invention further include control means for controlling the cutting means, the irradiating means, and the detecting means.

With the foregoing structure, an electrophoresis apparatus according to the present invention can realize highly automated two-dimensional electrophoresis.

With the present invention, sampling can be performed immediately after the electrophoresis. Further, the present invention can suppress or prevent problems such as drying or deformation of the gel, or spreading of separated protein spots.

For example, a sample contains different kinds of proteins: proteins that are abundant and have known molecular weights; and unknown proteins that are contained only in a small quantity. The present invention can easily eliminate abundant protein spots. The invention therefore prevents spreading of abundant protein spots, diffusion or scattering of high-intensity fluorescence, and thereby enables detection of weak fluorescence from proteins that are contained only in a small quantity.

The present invention can improve accuracy of analysis of detected fluorescence because the analysis is performed within an optimum range. Further, for example, from the proteins of various molecular weights in a sample, large molecular weight proteins, which are separated at the early stage of electrophoresis can be cut at the early stage of electrophoresis, with the result that protein spots with good separations can be collected and properly analyzed.

Therefore, in a brief and non-limiting overview of the preferred aspects of the invention, there is provided an electrophoresis device (100) including an insulator (10) that includes: a first-separating-medium storing section (4') for storing therein a first separating medium (4); a first opening (7) and a second opening (8) that are in communication with the first-separating-medium storing section (4') and for defining a direction of separation on the first separating medium (4); and a third opening (9) that is covered with a penetrable insulating thin film (3), wherein the first separating medium storing section (4') is in communication with outside via the first opening (7) and the second opening (8). There is also provided an electrophoresis apparatus including the electrophoresis device (100). This realizes an electrophoresis apparatus, and a device therefor, that enables an operator to sample separated proteins without ever making contact with the electrophoresed gel, and that can easily be used with various types of analyses, thereby improving convenience of electrophoresis.

REFERENCE NUMERALS

1: lower substrate (first plate-insulator)
2: upper substrate (second plate-insulator)
3: resin film (insulating thin film)
4: 2D gel (first separating medium)
4': slit portion (first-separating-medium storing section)
5: first buffer chamber
6: second buffer chamber
7: first opening
8: second opening
9: third opening
10: insulator
20: cutting means
30: irradiating means
40: detecting means
50: first voltage applying means
51: first wiring means
52: first electrode
53: second electrode
60: stage (fixing substrate)

70: 1D cell (separating device)
71: 1D separating chamber
72: 1D gel (second separating medium)
73: supporting plate
74: gel-equipped supporting plate
80: second voltage applying means
81: second wiring means
82: third electrode
90: arm
100: 2D cell (electrophoresis device)
200: electrophoresis apparatus
201: two-dimensional electrophoresis apparatus

BEST MODE FOR CARRYING OUT THE
INVENTION

With reference to FIG. 1 through FIG. 4, the following will describe a first embodiment of an electrophoresis device according to the present invention. As an example, description will be made based on an electrophoresis device 100 that can be used as a 2D chip for two-dimensional electrophoresis (second-electrophoresis chip).

Figure 1:
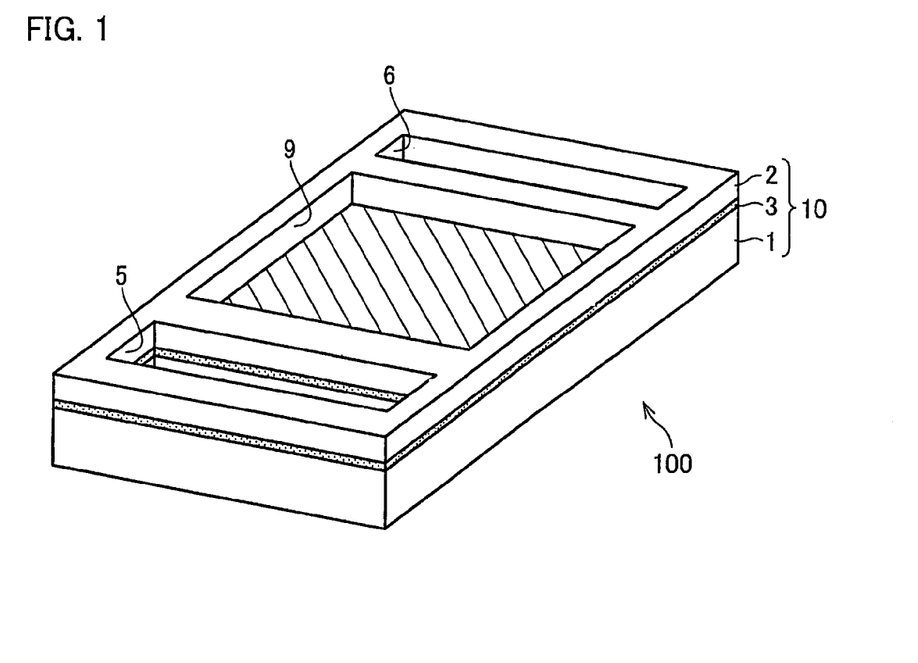
FIG. 1 is a perspective view showing a main structure of an electrophoresis device according to one embodiment of the present invention.
Figure 2:
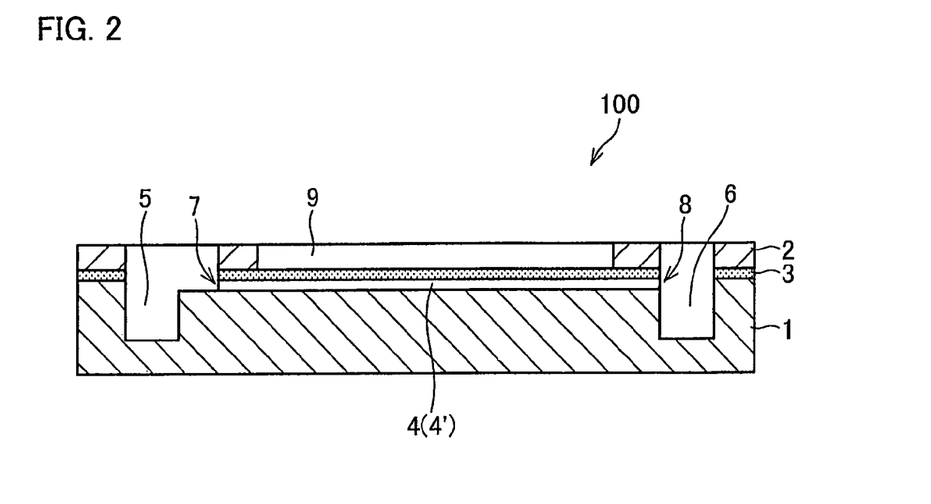
FIG. 2 is a cross sectional view showing a main structure of the electrophoresis device according to one embodiment of the present invention.

FIG. 1 is a perspective view illustrating a main structure of the electrophoresis device 100 according to one embodiment of the present invention. The electrophoresis device 100 of the present embodiment includes an insulator 10 formed of a lower substrate (first plate-insulator) 1, an upper substrate (second plate-insulator) 2, and a resin film (insulating thin film) 3 provided between the lower substrate 1 and the upper substrate 2. The insulator 10 is provided with a slit portion (first-separating-medium storing section) 4' that stores a first separating medium 4 to be subjected to the second electrophoresis. The insulator 10 also includes a first buffer chamber 5, a second buffer chamber 6, and a third opening 9. FIG. 2 is a cross section of the electrophoresis device 100 shown in FIG. 1.

Figure 3:
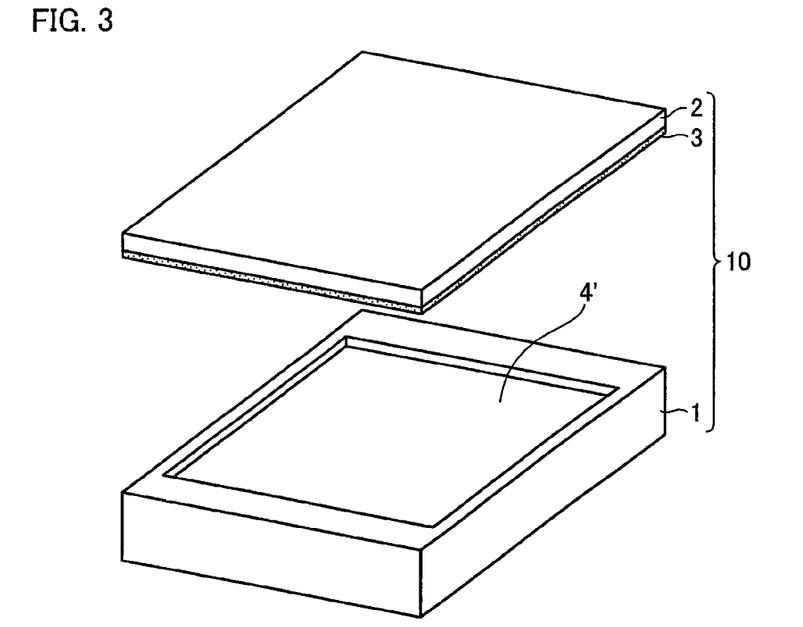
FIG. 3 is a schematic view depicting a main structure of the electrophoresis device according to one embodiment of the present invention.
Figure 4:
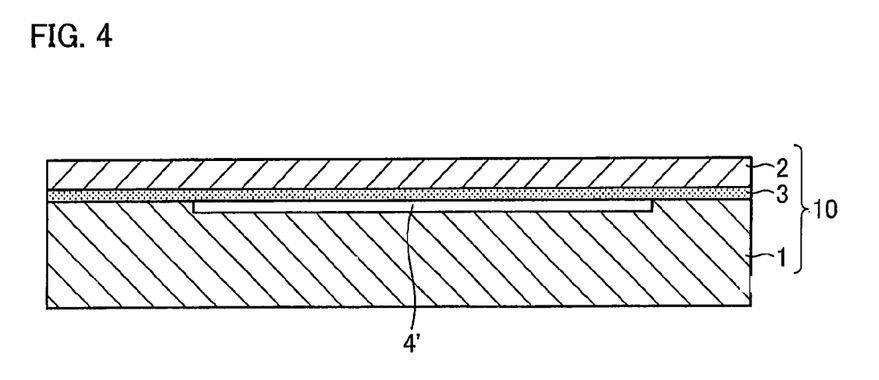
FIG. 4 is a cross sectional view depicting a main structure of the electrophoresis device according to one embodiment of the present invention.

With reference to FIGS. 3 and 4, the following will describe procedures for fabricating the electrophoreses device shown in FIGS. 1 and 2.

The lower substrate 1 with the slit portion 4' on its upper surface is combined with the upper substrate 2 having attached thereon the resin film 3, so that the insulator 10 covers the slit portion 4'. Thereafter, two grooves (first buffer chamber 5 and second buffer chamber 6) are formed in the lower substrate 1, penetrating through the upper substrate 2. The first separating medium 4 stored in the first-separating-medium storing section 4' is in communication with outside of the insulator 10 through a first opening 7 and a second opening 8. In the third opening 9 provided in the upper substrate 2, the first separating medium 4 in the insulator 10 is isolated from outside by the resin film 3.

The first opening 7 and the second opening 8 face the first buffer chamber 5 and the second buffer chamber 6, respectively, of the electrophoresis device 100. For sample separation, the first buffer chamber 5 and the second buffer chamber 6 are filled with a first buffer and a second buffer, respectively, which, at the first opening 7 and the second opening 8, are in contact with the first separating medium 4 stored in the slit portion 4' (not shown).

The term "sample" is a synonym for a specimen or a preparation in the art. As used herein, the "sample" refers to a "biological sample" or its equivalents. The "biological sample" means any preparation obtained from source biological materials (for example, individual organisms, body fluids, cell lines, cultured tissues, or tissue sections). Examples of such biological samples include body fluids (for example, blood, saliva, plaque, serum, blood plasma, urine, synovial fluid, and spinal fluid), and tissues. Preferably, biological samples are samples obtained from subjects. Such subject samples are preferably skin lesions, pharyngeal mucus, nasal mucus, pus, or secreted material. As used herein, "tissue samples" are intended to mean biological samples obtained from tissues. Methods of obtaining tissue samples and body fluids from mammals are known in the art. As used herein, the meaning of "sample" is not just limited to the biological samples and tissues samples as defined above, but it also encompasses protein samples, genomic DNA samples, and/or total RNA samples extracted from the biological samples and tissue samples.

Figure 10:
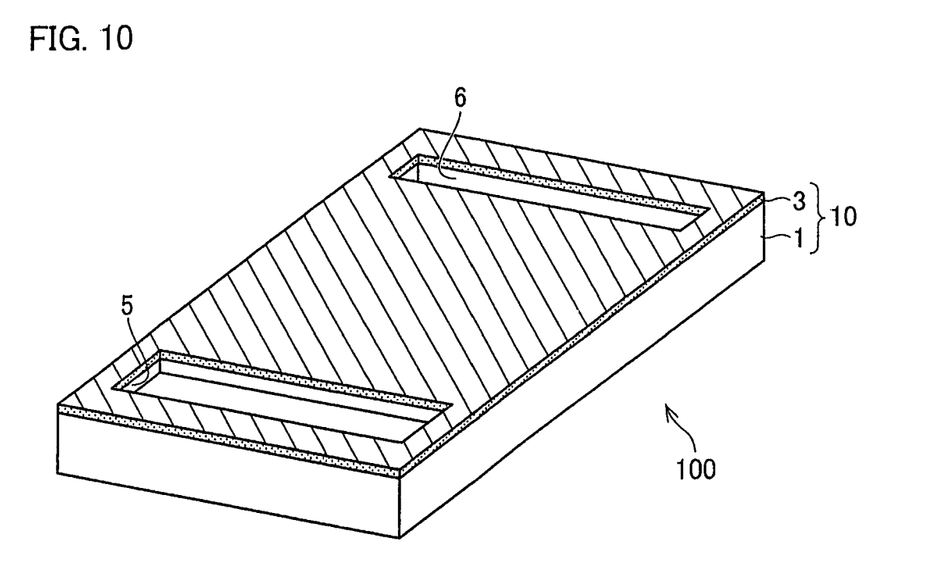
FIG. 10 is a perspective view showing a main structure of an electrophoresis device according to one embodiment of the present invention.
Figure 11:
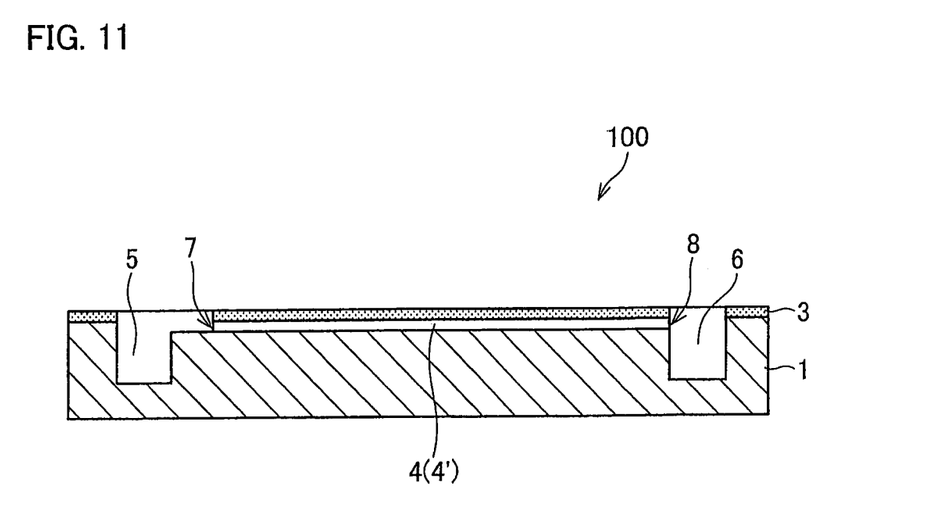
FIG. 11 is a cross sectional view showing a main structure of the electrophoresis device according to one embodiment of the present invention.

In the structure described above, the electrophoresis device 100 has the upper substrate 2 and the resin film 3 attached together. However, the resin film 3 may be attached to the lower substrate 1 provided with the groove portion 4', or may be separately provided from the upper substrate 2. Further, the insulator 10 may be formed of the lower substrate 1 and the resin film 3, without using the upper substrate 2, as shown in FIGS. 10 and 11.

In the case where the insulator 10 is formed of the lower substrate 1 and the resin film 3, it is preferable that the groove portion 4' stores the first separating medium 4 in advance. In FIG. 2, the resin film 3 has been removed in portions corresponding to the first buffer chamber 5 and the second buffer chamber 6. However, these portions of the resin film 3 may be removed immediately before the electrophoresis device 100 is used. This enables the resin film 3 to completely cover the electrophoresis device 100 that has stored the first separating medium 4 and the buffers, and therefore allows the electrophoresis device 100 to be preserved with reagents contained therein.

In the case where the first separating medium 4 stored in the groove portion 4' has been prepared separately outside of the electrophoresis device 100, the upper substrate 2 and the resin film 3 are preferably attached together from the view point of operability. As in the foregoing case, the resin film 3 may be provided without the upper substrate 2.

In any case, in the electrophoresis device, current needs to be flown from the second opening 8 to the first opening 7. To this end, the insulator 10 needs to be in contact with the first separating medium 4 and insulate the first separating medium 4, except at the first opening 7 and the second opening 8. Further, since the liquid (buffers) needs to be retained in the first buffer chamber 5 and the second buffer chamber 6, the insulator 10 is preferably made waterproof. Non-limiting examples of such insulating materials include polyethylene terephthalate, polyvinylchloride, and polyvinylidene chloride.

Figure 5:
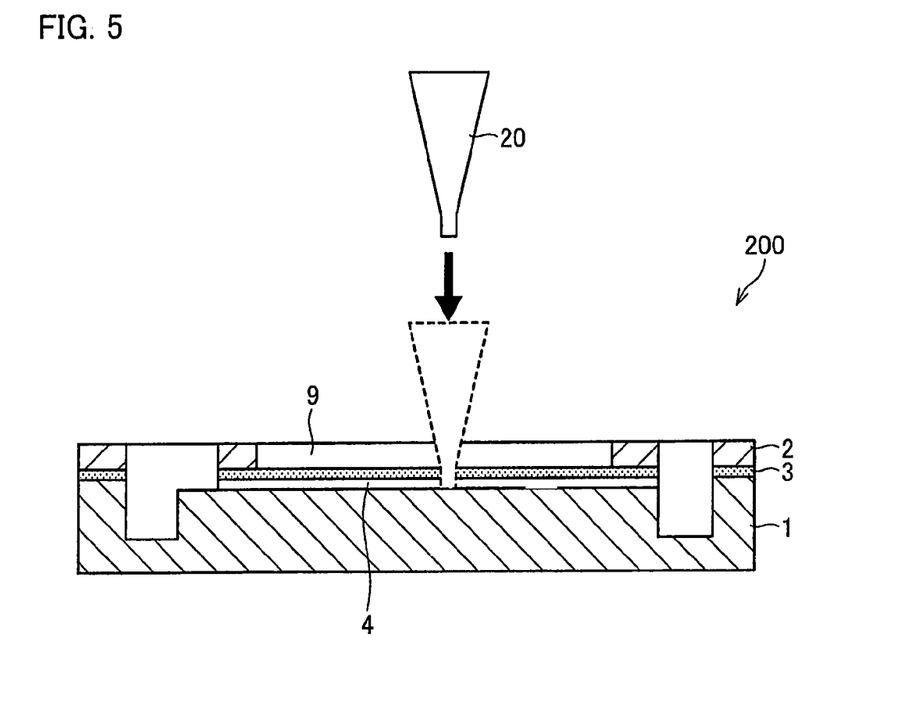
FIG. 5 is a cross sectional view showing a main structure of an automated two-dimensional electrophoresis apparatus according to one embodiment of the present invention.

In order for the desired protein (or DNA, etc.) bands in the first separating medium 4 to be cut out with cutting means 20 as shown in FIG. 5, the cutting means 20 needs to properly cut through the resin film 3. To this end, the resin film 3 is preferably a resin thin film that can be cut through with a hollow bowl structure, and preferably has a thickness no greater than 125 μm, or more preferably a thickness in a range of 30 μm to 125 μm. Further, the resin film 3 is preferably a resin thin film that can be struck through with a hollow bowl structure having a tip diameter no greater than 5 mm. More preferably, the resin film 3 has a strike resistance of 1 mN to 50 mN.

When the protein (or DNA, etc.) of interest is fluorescence-labeled (or fluorescence-stained), fluorescence of the protein (or DNA, etc.) bands needs to be detected. In order for the protein (or DNA, etc.) to fluoresce, excitation light needs to have access to the protein (or DNA, etc.), and the generated fluorescence needs to be released out of the first separating medium. Thus, the insulator 10 needs to be provided with a light-transmissive portion through which the excitation light and fluorescence can transmit. The light-transmissive portion is made of a light-transmissive material, and has a transmittance preferably no less than 80%, more preferably no less than 85%, and most preferably no less than 90%. The light-transmissive portion formed in the insulator 10 may be provided only in a portion of the lower substrate 1 or the insulating thin film 3, or the insulator 10 may be entirely made of a light-transmissive material.

Figure 6:
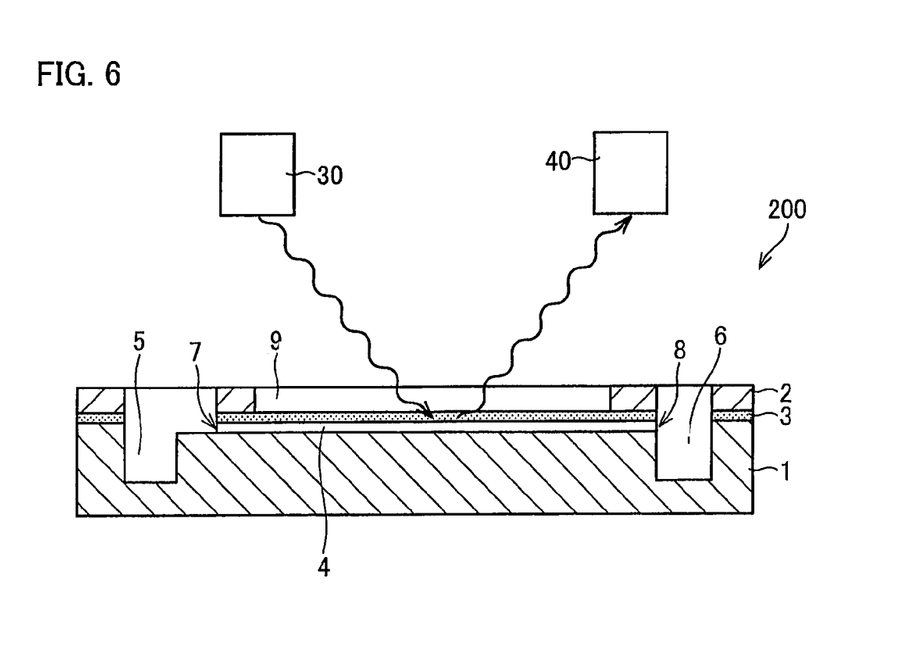
FIG. 6 is a cross sectional view showing a main structure of the automated two-dimensional electrophoresis apparatus according to one embodiment of the present invention.

The irradiating means 30 for irradiating excitation light on the fluorescence-label of the protein (or DNA, etc.), and the detecting means 40 for detecting the fluorescence emitted by the fluorescence material labeling the protein (or DNA, etc.) can be suitably positioned. However, it is preferable that the irradiating means 30 and the detecting means 40 be provided above the first separating medium 4, as shown in FIG. 6. It is therefore highly preferable that the resin film 3 be light-transmissive. As shown in FIG. 6, the light emitted by the irradiating means 30 transmits through the resin film 3 and irradiates the first separating medium 4. In response, a sample in the first separating medium 4 fluoresces, and the detecting means 40 detects the fluorescence. If the lower substrate 1 were light-transmissive, the irradiating means 30 and the detecting means 40 may be provided beneath the lower substrate 1 and the detection of the fluorescence emitted by the fluorescence material labeling the protein (or DNA, etc.) may be made by these irradiating means 30 and detecting means 40.

Since the first separating medium 4 is preferably in contact with the buffers only at the first opening 7 and the second opening 8, the insulator 10 covering the first separating medium 4 is preferably made of a highly water-proof material.

Considering the above, the insulator 10 is preferably made of glass or resin, for example. Examples of resin materials include acrylic resin, polydimethyl siloxane (PDMS), polyolefin resin, polycarbonate, polystyrene, polyethylene terephthalate (PET), and polyvinyl chloride. Among these examples, acrylic resin (polymethylmethacrylate (PMMA), for example) is preferable in terms of weight, operability, and productivity. The resin film 3 used in the present invention is preferably made of polyethylene terephthalate, polyvinylchloride, and polyvinylidene chloride. However, the material of the resin film 3 is not just limited to these examples. When the resin film 3 itself is transmissive, the resin film 3 is preferably uses a resin that is designed as an optical material. For example, in this case, the resin film 3 is preferably made of acrylic resin or polyolefin resin.

Though the invention has been described based on the electrophoresis device 100 in which the insulator 10, the first buffer chamber 5, and the second buffer chamber 6 are formed in one piece, these members may be separate components. The first separating medium 4 may be formed directly in the first-separating-medium storing section 4', or formed separately and fixed on the first-separating-medium storing section 4'. The first-separating-medium storing section 4' is not necessarily required to be a slit. In this case, spacers (not shown) having the same thickness as the first separating medium 4 are placed around portions of the lower substrate 1 where the fist separating medium 4 is to be fixed, and the lower substrate 1 and the upper substrate 2 are bonded together via the spacers.

As described above, according to one aspect of the present invention, there is provided an electrophoresis device including: a lower substrate retaining the first separating medium; and a first buffer chamber and a second buffer chamber for reserving buffers at the both ends of the lower substrate, the lower substrate including the upper substrate thereon, and the upper substrate being a resin film.

According to another aspect of the present invention, there is provided an electrophoresis device including: a lower substrate retaining the first separating medium; and a first buffer chamber and a second buffer chamber for reserving buffers at the both ends of the lower substrate, the first separating medium on the lower substrate being covered with a resin film.

In this manner, in the present invention, a thin film covers a surface that is in contact with the separating medium where separated protein spots are obtained.

In an electrophoresis device according to the present invention, it is preferable that the resin film have a thickness no greater than 125 µm, and a strike resistance of 1 mN to 50 mN.

According to the foregoing structure, an electrophoresis device according to the present invention can collect the gel (protein spot) by striking through the thin film with the hollow bowl structure.

In an electrophoresis device according to the present invention, it is preferable that the first separating medium be a gel material.

Further, the present invention does not require removing the gel. This prevents the gel form being dried and/or deformed, and allows for analysis on a low noise background without washing the gel, which is necessitated when the gel is removed.

At the end of voltage application (when the electrophoresis is finished), an end marker of electrophoresis, such as a pigment marker, a dye, or a fluorescent pigment that failed to label the sample has been separated on one end of the gel (low molecular weight side). By thus preventing these substances from contacting the gel after the sample separation, the analysis can be made without errors.

Further, the present invention allows for sampling as a function of time while observing the sample, thereby realizing accurate, fast, and mass sampling. Further, a part of the gel can be cut out during the electrophoresis.

Further, since abundant protein (or DNA) spots can be removed at the end of voltage application (at the end of electrophoresis), the invention easily allows for detection of micro spots.

Figure 7:
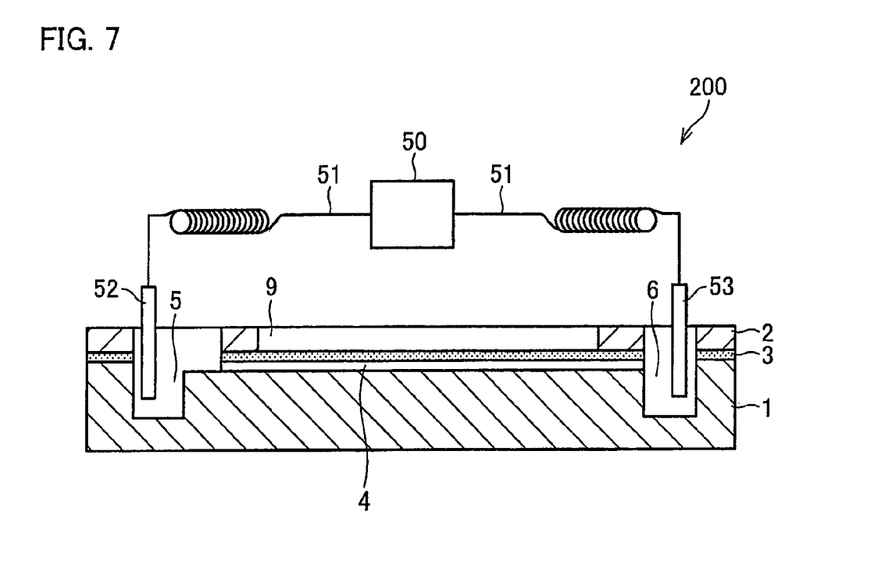
FIG. 7 is a cross sectional view showing a main structure of the automated two-dimensional electrophoresis apparatus according to one embodiment of the present invention.

With reference to FIG. 5 through FIG. 7, the following will describe one embodiment of an electrophoresis apparatus according to the present invention.

FIG. 5 shows a main structure of an electrophoresis apparatus 200 according to one embodiment of the present invention. The electrophoresis apparatus 200 according to the present embodiment includes an electrophoresis device 100 and cutting means 20. The electrophoresis device 100 includes an insulator 10 formed of a lower substrate 1, an upper substrate 2, and a resin film 3 provided between the lower substrate 1 and the upper substrate 2. The insulator 10 is provided with a slit portion 4' storing a first separating medium 4 on which the second electrophoresis is performed. In other words, the first separating medium 4 is covered with the resin film 3.

The cutting means 20 is movable in three directions with the aid of moving means (not shown) provided in the electrophoresis apparatus 200. As shown in FIG. 5, the cutting means 20 moves in a direction of Z axis (direction of arrow in FIG. 5) through the resin film 3 covering the first separating medium 4, and strikes the first separating medium 4 to collect desired protein (or DNA, etc.) bands. As described above, the cutting means 2 needs to properly cut through desired protein (or DNA, etc.) bands in the first separating medium 4. To this end, the resin film 3 is preferably a resin thin film that can be cut through with a hollow bowl structure, and preferably has a thickness no greater than 125 µm, or more preferably in a range of 30 µm to 125 µm. Further, the resin film 3 is preferably a resin thin film that can be struck through with a hollow bowl structure having a tip diameter of no greater than 5 mm. More preferably, the resin film 3 has a strike resistance of 1 mN to 50 mN. With such structure, an operator can avoid contacting the gel in using the electrophoresis apparatus 200. Further, an operator can pause voltage application during the electrophoresis, and can resume the procedure by applying the voltage again after sampling part of the proteins (or DNA, etc.).

The electrophoresis apparatus 200 according to the present invention includes control means (not shown) for properly controlling operations of the cutting means 20, the irradiating means 30, and the detecting means 40, and processing collected data. The control means according to the present embodiment includes a control unit with a plurality of functional elements, such as an arithmetic section, a memory section, and a processing section. The memory section of the control means stores a program that executes the arithmetic operations performed by the processing section. The memory section also stores collected data, which is supplied to the processing section as required. The control is realized as the control unit causes the arithmetic section to execute the program stored in the memory section and thereby controls an input/output circuit and other peripheral circuits (not shown). Non-limiting examples of such peripheral circuits include: a storing section for storing various pre-set values (for example, excitation wavelength/fluorescence wavelength of the fluorescence material used); a comparing section for comparing detected values with the stored values; and a circuit provided between, for example, processing sections which, based on the result of comparison, calculate an output used to control the moving means or the cutting means. All of these functional blocks are under the control of the arithmetic sections. Specific structures and functions of these functional blocks are not particularly limited.

In the electrophoresis actually performed by the electrophoresis device 100, first voltage applying means 50 applies voltages to the first separating medium 4 via a first electrode 52 and a second electrode 53 respectively inserted in the first buffer chamber 5 and the second buffer chamber 6, as shown in FIG. 7. As a result, current is flown through the second opening 8 toward the first opening 7, and the sample that has been applied on the first separating medium 4 develops/separates as it moves from the first opening 7 toward the second opening 8.

In the electrophoresis apparatus 200 according to the present embodiment, the first electrode 52 and the second electrode 53, respectively inserted in the first buffer chamber 5 and the second buffer chamber 6, are connected to the first voltage applying means 50 via wiring means 51. The first electrode 52 and the second electrode 53 may be fixed on the first buffer chamber 5 and the second buffer chamber 6, respectively. However, considering that the first electrode 52 and the second electrode 53 are replaced for each different sample using the electrophoresis device 102, it is more preferable not to fix the first electrode 52 and the second electrode 53. In the case where the wiring means 51 is movable by the moving means (not shown), the first electrode 52 and the second electrode 53 may be detachably provided on electrode fixing sections (not shown) respectively provided for the first buffer chamber 5 and the second buffer chamber 6. Further, as shown in FIG. 7, the first electrode 52 and the second electrode 53 may simply be inserted in the buffers respectively filling the first buffer chamber 5 and the second buffer chamber 6.

When the first electrode 52 and the second electrode 53 are not fixed and are movable, it is easier to wash the first electrode 52 and the second electrode 53.

Figure 8:
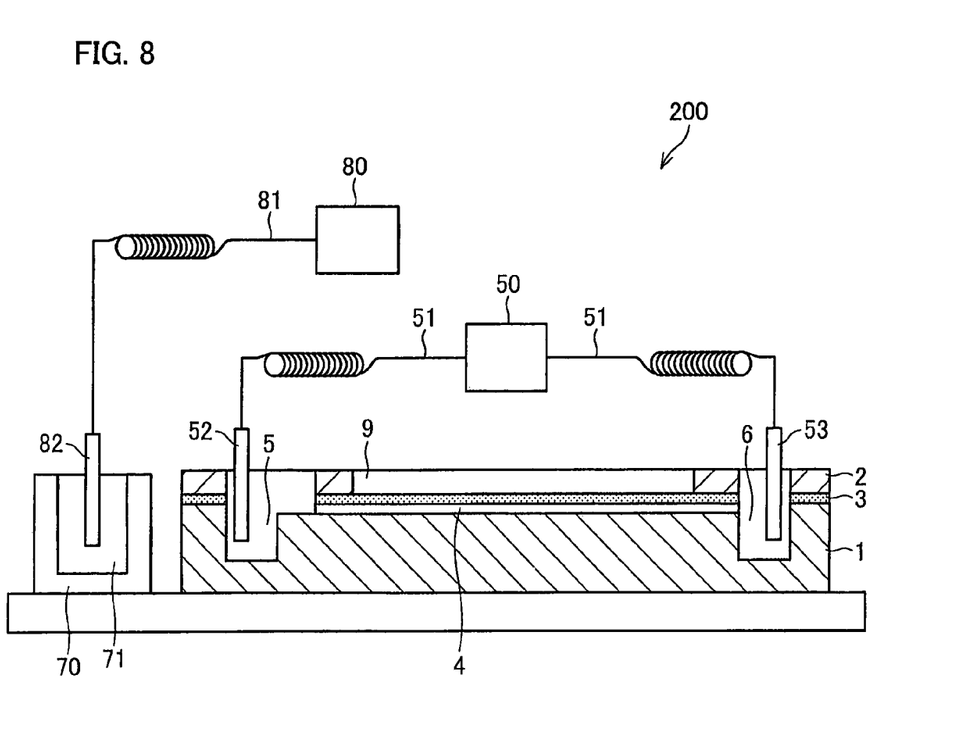
FIG. 8 is a cross sectional view showing a main structure of the automated two-dimensional electrophoresis apparatus according to one embodiment of the present invention.
Figure 9:
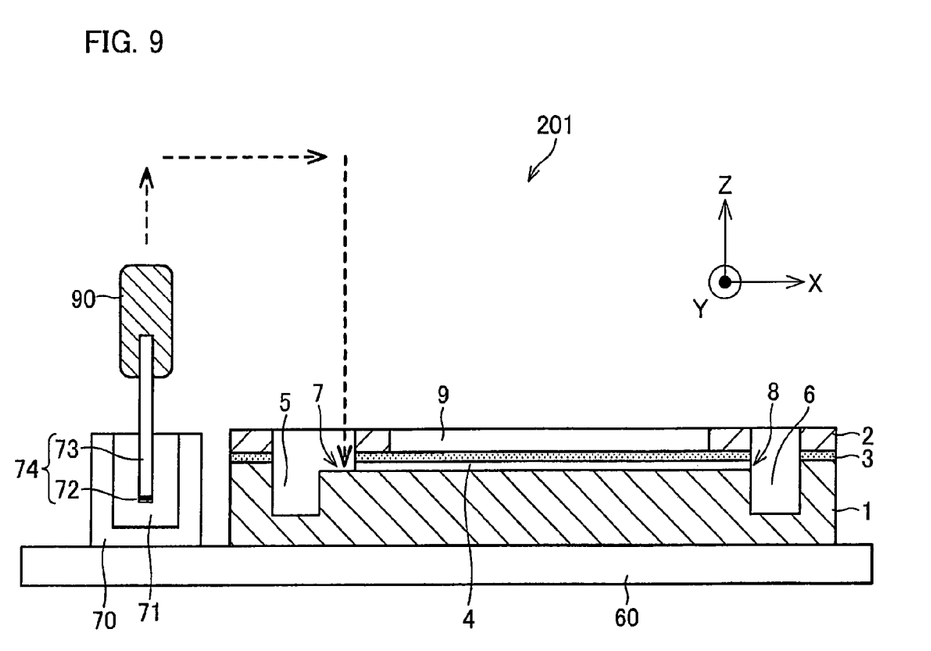
FIG. 9 is a cross sectional view showing a main structure of an automated two-dimensional electrophoresis apparatus according to one embodiment of the present invention.

With reference to FIG. 8 and FIG. 9, the following will describe another embodiment of the present invention, based on a two-dimensional electrophoresis apparatus 201.

FIG. 8 shows a main structure of the two-dimensional electrophoresis apparatus 201 according to one embodiment of the present invention. The two-dimensional electrophoresis apparatus 201 according to the present embodiment includes a 2D cell (electrophoresis device) 100 and a 1D cell (separating device) 70. The 2D cell 100 includes an insulator 10 formed of a lower substrate 1, an upper substrate 2, and a resin film 3 provided between the lower substrate 1 and the upper substrate 2. The insulator 10 includes a slit portion 4' storing a first separating medium 4. In other words, the first separating medium 4 is covered with the resin film 3.

In the electrophoresis apparatus 201, the 1D cell 70 includes a 1D separating chamber 71 where the electrophoresis is actually performed. In the 1D separating chamber 71, second voltage applying means 80 applies voltage to a 1D gel (second separating medium) (not shown) via a third electrode 82, as shown in FIG. 8. As a result, the sample that has been applied to the 1D gel develops/separates in the direction perpendicular to the plane of paper in FIG. 8.

In the two-dimensional electrophoresis apparatus 201 according to the present embodiment, the first electrode 52 and the second electrode 53 are connected to the first voltage applying means 50 via the wiring means 50, and the third electrode 82 is connected to the second voltage applying means 80 via second wiring means 81.

The first electrode 52 and the second electrode 53 may be fixed on the first buffer chamber 5 and the second buffer chamber 6, respectively. However, considering that the first electrode 52 and the second electrode 53 are replaced for each different sample using the 2D cell 100, it is more preferable not to fix the first electrode 52 and the second electrode 53. In the case where the wiring means 51 is movable by the moving means (not shown), the first electrode 52 and the second electrode 53 may be detachably provided on electrode fixing sections (not shown) respectively provided for the first buffer chamber 5 and the second buffer chamber 6. Further, as shown in FIG. 8, the first electrode 52 and the second electrode 53 may simply be inserted in the buffers filling the first buffer chamber 5 and the second buffer chamber 6, respectively.

As with the first electrode 52 and the second electrode 53, the third electrode 82 may be fixed on the 1D separating chamber 71. However, considering that the third electrode 82 is replaced for each different sample using the 1D cell 70 and the 2D cell 100, it is more preferable not to fix the third electrode 82. In the case where the wiring means 51 is movable by the moving means (not shown), the third electrode 82 may be detachably provided on an electrode fixing section (not shown) provided for the 1D separating chamber 71. Further, as shown in FIG. 8, the third electrode 82 may simply be inserted in the buffer filling the 1D separating chamber 71.

It is easier to wash the first electrode 52, the second electrode 53, and the third electrode 82 when these electrodes are movable rather than being fixed. Further, for automation of the apparatus, the 1D cell 70 and the 2D cell 100 should preferably be fixed on a stage (fixing substrate) 60.

FIG. 9 illustrates a main part of a structure for automating the steps performed by the two-dimensional electrophoresis apparatus 201 according to the present embodiment. In the two-dimensional electrophoresis apparatus 201, the 1D cell 70 and the 2D cell 100 are provided on the stage 60. In the 2D cell 100, the slit portion 4' of the insulator 10, including the lower substrate 1, the upper substrate 2, and the resin film 3 provided between the lower substrate 1 and the upper substrate 2, stores the first separating medium 4 on which the two-dimensional electrophoresis is performed. That is, the first separating medium 4 is covered with the resin film 3.

As shown in FIG. 9, a 1D gel 72 and a support plate 73 are bonded together to form a gel-equipped support plate 74. The 1D gel, which is commercially available, has a transparent resin sheet, 0.2 mm thick, attached on the rear surface. The 1D gel 72 is bonded to the support plate 73 on this sheet portion, using an adhesive. Here, any adhesive known in the art can be used. However, since the 1D gel 72 bonded with the support plate 73 should preferably be preserved at low temperatures (−20° C.) till it is used, it is preferable to use an adhesive that is suited for low-temperature preservation. Such temperature characteristics are also desired for the support plate 73. The support plate 73 is held by an arm 90 that is driven by the moving means (not shown) of the two-dimensional electrophoresis apparatus 201 according to the present embodiment. By the moving means (not shown), the arm 90 is movable along X direction and/or Z direction, as shown in FIG. 9.

In the first buffer chamber 5, the opening made through the upper substrate 2 is greater in width than the corresponding groove formed in the lower substrate 1. By the width difference, a sample supply opening is formed where the 1D gel 72 is brought into contact with the 2D gel 4, enabling the second separation to be properly performed on the sample in the 1D gel 72 that has undergone the first separation in the 1D separating chamber 71. In the present embodiment, the first opening 7 serves as the sample supply opening, as shown in FIG. 9.

As shown in FIG. 9, two-dimensional electrophoresis is performed from left to right. The following will describe each step performed by the two-dimensional electrophoresis apparatus 201.

First, all the samples, reagents, and separating medium required for the two-dimensional electrophoresis are set in predetermined positions, and the control means (not shown) appropriately controls respective means of the two-dimensional electrophoresis apparatus 201 to perform each step by automation. Under the control of the control means, the moving means (not shown) is driven to move (transport) the arm 90 and thereby indirectly move (transport) the 1D gel 72.

The 1D gel 72, having been subjected to necessary treatment for the first sample separation is transported to the second separating chamber 71 and placed between the third electrodes 82 therein. Here, the second voltage applying means 80 applies voltage to the 1D gel 72 and the sample in the 1D gel 72 is separated in the first direction. Information concerning time and voltage required for sample separation is stored in the storing section of the control means. The information is suitably selected and executed according to the program stored in the storing section of the control means, depending on the types of 1D gel 72, samples, and reagents used.

After the separation in the first direction has been finished in the 1D gel 72, the 1D gel 72 is transported by the moving means to a predetermined position where the 1D gel 72 is subjected to a necessary post-treatment of the first sample separation (prior to the second sample separation). As required, the 1D gel 72 is shaken gently. After the treatment, the 1D gel 72 is transported by the moving means to the sample supply opening 7 of the 2D gel 4, where the 1D gel 72 is brought into contact with the 2D gel 4.

With the 1D gel 72 in contact with the 2D gel 4, the first voltage applying means 50 applies voltage to the 2D gel 4. As a result, the sample that has been separated in the first direction in the 1D gel 72 is further separated in the 2D gel 4 in the second direction (to the right along the X axis), different from the first direction (Y direction). In order to realize the sample separation in the second direction, the following steps are performed in the 2D cell 4: a step in which the sample that has been separated in the first direction is brought into contact with the 2D gel 4; a step in which voltage is applied to the 2D gel 74 to separate the sample in the second direction; and a step in which the sample is detected as it is being separated in the second direction.

Time and other necessary information for the separation in the 2D gel 4 is also stored in the storing section of the control means. The information is suitably selected and executed according to the program stored in the storing section of the control means, depending on the types of 2D gel 4, samples, and reagents used.

The irradiating means 30 and the detecting means 40 allow the state of sample separation to be sensitively analyzed while the sample is being separated in the second direction, after or during the electrophoresis. As required, voltage application to the 2D gel 4 by the first voltage applying means 50 is stopped, and fluorescence-labeled protein (or DNA, etc.) spots or bands at target positions are cut by the cutting means 20.

The storing section of the control means also stores information such as characteristics of the fluorescence material used. The information is suitably selected and executed according to the program stored in the storing section of the control means, depending on the types of 1D gel 72 and 2D gel 4, the types of lower substrate 1 and/or resin film 3, the type of light absorbing layer 9, the type of sample, and the type of reagent.

In the two-dimensional electrophoresis apparatus 201, the sample is separated in the first direction in the 1D gel 72, and in the second direction in the 2D gel 4. The parameters that define the separation may be the same in the first direction and the second direction. However, for improved separation, it is preferable to set different parameters for the first direction and the second direction. Examples of parameters that define the separation in these two directions include: an isoelectric point of protein; molecular weight; surface charge (zone electrophoresis) per unit size; distribution coefficient for a micelle (micelle electrokinetic chromatography); distribution coefficient for stationary phase-mobile phase (electrical chromatography); and affinity constant for interacting substances (affinity coupling electrophoresis). Common two-dimensional electrophoresis uses an isoelectric point for the separation in the first direction, and a molecular weight for the separation in the second direction.

Considering that the 1D cell 70 and the 2D cell 100 are replaced for each different sample, it is preferable that the 1D cell 70 and the 2D cell 100 be fixed detachably. The mechanism for fixing the 1D cell 70 and the 2D cell 100 on the stage (fixing substrate) 60 may be, but are not limited to, a vacuum suction mechanism, a narrow fixing mechanism, a magnetic force fixing mechanism, or an electrostatic absorption mechanism. Similarly, it is preferable that the gel-equipped support plate 74 be detachably held by the arm 90. When using a vacuum suction mechanism, it is preferable that the 1D cell 70 and the 2D cell 100 be fixed via a vacuum suction plate (not shown).

In the electrophoresis apparatus 201, three-dimensional position accuracy of the gel-equipped plate 74 is important.

Under the control of the control means (not shown) provided in the electrophoresis apparatus 201, the arm 90 is accurately moved to accurately perform various steps on the 1D gel 72. In the case where the electrodes 52, 53, and 82 are transported/fixed by automation, the arm 90 may be adapted to transport/fix the electrodes 52, 53, and 82 to/on the first buffer chamber 5, the second buffer chamber 6, and the 1D separating chamber 71, respectively, under the control of the control means.

Since the electrophoresis is performed under high voltage, the 1D cell 70 and the 2D cell 100 rise to high temperatures during sample separation. For this reason, the two-dimensional electrophoresis apparatus 201 is provided with cooling means (not shown), directly below the stage 60, for cooling the 1D cell 70, the 2D cell 100, and the stage 60 on which the 1D cell 70 and the 2D cell 100 are fixed. Specifically, in the two-dimensional electrophoresis apparatus 201, the temperatures of the 1D cell 70 and the 2D cell 100 can be maintained constant during electrophoresis, by the provision of Peltier cooling control mechanism.

Further, the two-dimensional electrophoresis apparatus 201 according to the present invention may further include, for example, temperature control means (not shown) for controlling temperatures of the 1D gel 72 and the 2D gel 4. In this way, a more sophisticated sample separation is possible, though not shown.

As described above, in the two-dimensional electrophoresis apparatus 201, the steps of the two-dimensional electrophoresis can be performed by full automation under the control of the control means. Further, by the provision of the control means capable of executing the foregoing control, the two-dimensional electrophoresis apparatus 201 allows for easy selection and/or adoption of various protocols to pursue optimum sample separating performance. Further, a two-dimensional high-voltage application control system may be adopted that causes a computer to perform feedback control of a voltage application program for two-dimensional electrophoresis, and this system may be controlled along with the automated stage.

As described above, according to one aspect of the invention, there is provided an electrophoresis apparatus, which include: a lower substrate for retaining the first separating medium; a first buffer chamber and a second buffer chamber, provided on the both ends of the lower substrate, respectively including a first electrode and a second electrode and reserving buffers; and an upper substrate, formed of a resin film, provided on the first separating medium that is retained by the lower substrate, the first buffer chamber and the second buffer chamber being filled with buffers.

In an electrophoresis apparatus according to the present invention, it is preferable that the resin thin film have a thickness no greater than 125 µm, and have a strike resistance of 1 mN to 50 mN.

In an electrophoresis apparatus according to the present invention, the irradiating means and the fluorescence detecting means are provided preferably above the upper substrate.

In an electrophoresis apparatus according to the present invention, the first separating medium is preferably a gel material.

With the human genome project proceeded to completion, there has been active research in proteomes. By "proteomes," it encompasses all proteins translated in specific cells, organs, and internal organs. One area of proteome research is protein profiling.

A technique that is most commonly used for protein profiling is the two-dimensional electrophoresis of protein. Proteins have unique properties in charge and molecular weight. Therefore, the resolution of protein separation can be improved for large numbers of proteins if individual proteins in the proteome, which is a collection of large numbers of proteins, were separated based on a combination of charge and molecular weight, rather than charge or molecular weight alone.

The two-dimensional electrophoresis is a two-step process. The first step is the isoelectric point electrophoresis in which proteins are separated based on charge. The second step is the slab gel electrophoresis (particularly, SDS-PAGE), in which proteins are separated based on molecular weight. The two-dimensional electrophoresis is a superior technique in the sense that it can be performed in the presence or absence of a denaturing agent for the sample, and that it can separate more than several hundred kinds of proteins at once.

The two-dimensional electrophoresis proceeds by performing the isoelectric point electrophoresis for the sample on the first gel. This is followed by taking out the first gel and applying it onto the second gel, where the second separation is made based on molecular weight. Generally, the first gel used for the isoelectric electrophoresis is considerably thin, relative to width and length. This makes it difficult to distinguish the front and the back of the gel, or identify the direction of pH gradient. Further, since the first gel with such profiles is prone to bending or twisting, it is difficult to maintain the shape of the gel constant. This can cause problems in reproducibility of electrophoresis results. Further, the first gel is not easy to handle, and it is difficult to improve position accuracy in applying the first gel onto the second gel.

As described thus far, while the two-dimensional electrophoresis is a superior technique, it requires skill. Because it is skill dependent, it is difficult in the two-dimensional electrophoresis to yield quantitative data with good reproducibility.

With the present invention, however, the steps of the two-dimensional electrophoresis can be carried out by full automation, and quantitative data can be obtained with good reproducibility.

The foregoing detailed description described the present invention in relation to the electrophoresis device and the electrophoresis apparatus. However, it will be apparent by a person ordinary skill in the art that the invention also provides a method for separating proteins (electrophoresis method for proteins).

Specifically, according to one aspect of the present invention, the invention provides a method for separating proteins, including the steps of:

having a lower substrate retain a first separating medium that includes a fluorescence-stained protein reagent, the lower substrate being provided in an electrophoresis device that includes a first buffer chamber and a second buffer chamber, provided on the both ends of the lower substrate, for reserving buffers;

placing an upper substrate, formed of a resin film, on the first separating medium;

filling the first buffer chamber and the second buffer chamber with buffers;

placing a first electrode and a second electrode in the buffers on the lower substrate;

separating proteins by electrophoresis; and detecting the proteins as they are being separated or after having been separated, using irradiating means and detecting means that are provided above the upper substrate.

In a method for separating proteins according to the present invention, it is preferable that proteins be separated in the step of separating proteins, and, after fluorescence detection, the separating medium having separated therein desired proteins be struck with a collecting stylus through the film so as to be collected.

In a method for separating proteins according to the present invention, it is preferable that the resin thin film have a thickness no greater than 125 µm, and have a strike resistance of 1 mN to 50 mN.

In a method for separating proteins according to the present invention, it is preferable that the first separating medium be a gel material.

The embodiments of implementation discussed in the foregoing BEST MODE FOR CARRYING OUT THE INVENTION section serve solely to illustrate the technical details of the present invention, which should not be narrowly interpreted within the limits of such embodiments, but rather may be applied in many variations within the spirit of the present invention, provided such variations do not exceed the scope of the patent claims set forth below.

INDUSTRIAL APPLICABILITY

An electrophoresis device according to the present invention can overcome the disadvantages of electrophoresis apparatuses (two-dimensional electrophoresis apparatuses in particular) and advance the development of ongoing active proteome research. Further, since an electrophoresis device according to the present invention can be separately fabricated or marketed as a part or a component of an electrophoresis apparatus, it can boost the market in the field of machinery, chemistry, biology, or any other fields.

The invention claimed is:

1. An electrophoresis device comprising an insulator, wherein the insulator includes:
   a first-separating-medium storing section for storing therein a first separating medium;
   a first opening and a second opening that are in communication with the first-separating-medium storing section and for defining a direction of separation on the first separating medium; and
   a third opening that is covered with an insulating thin film that is penetrable for cutting out a sample in the first separating medium;
   wherein the insulator includes a first plate-insulator and the insulating thin film;
   wherein the first-separating-medium storing section is a depression formed in the first plate-insulator, and the first separating medium is covered with the insulating thin film; and
   wherein the insulator further comprises a second plate-insulator, and
   wherein the third opening is provided in the second plate-insulator.

2. The electrophoresis device as set forth in claim 1, wherein the first separating medium is stored in the first-separating-medium storing section.

3. The electrophoresis device as set forth in claim 1, further comprising:
   a first buffer chamber for reserving a first buffer to be brought into contact with the first separating medium at the first opening;
   a second buffer chamber for reserving a second buffer to be brought into contact with the first separating medium at the second opening
   a first movable electrode in the first buffer chamber; and
   a second movable electrode in the second buffer chamber.

4. The electrophoresis device as set forth in claim 3, wherein the insulator, the first buffer chamber, and the second buffer chamber are formed in one piece.

5. The electrophoresis device as set forth in claim 1, wherein the first opening or the second opening is shaped to fit a second separating medium retaining a sample.

6. The electrophoresis device as set forth in claim 5, wherein the first separating medium and the second separating medium have different separating parameters.

7. The electrophoresis device as set forth in claim 1, wherein the insulating thin film has a thickness no greater than 1000 µm.

8. The electrophoresis device as set forth in claim 1, wherein the insulating thin film has a strike resistance of 1 mN to 50 mN.

9. The electrophoresis device as set forth in claim 1, wherein the insulating thin film comprises any one of a polystyrene film, a polyethylene terephthalate film, a polyvinylchloride film, a polyvinylidene chloride film, polyolefin resin film, and a biaxial polypropylene film.

10. An electrophoresis apparatus comprising:
    an electrophoresis device of claim 1; and
    a cutter for cutting out a sample in the first separating medium.

11. The electrophoresis apparatus as set forth in claim 10, further comprising:
    an irradiator for irradiating a sample in the first separating medium; and
    a detector means for detecting fluorescence from the sample.

12. The electrophoresis device as set forth in claim 1, wherein the first plate-insulator or the insulating thin film is made of a light-transmissive material.

* * * * *